US00PP24605P3

(12) United States Plant Patent
Caster et al.

(10) Patent No.: US PP24,605 P3
(45) Date of Patent: Jul. 8, 2014

(54) BLUEBERRY PLANT NAMED 'DRISBLUESEVEN'

(50) Latin Name: ***Vaccinium corymbosum* L.**
Varietal Denomination: DrisBlueSeven

(75) Inventors: Brian K. Caster, Salinas, CA (US); Jennifer K. Izzo, Watsonville, CA (US); Arlen Draper, Payson, AZ (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 95 days.

(21) Appl. No.: 13/507,925

(22) Filed: Aug. 7, 2012

(65) Prior Publication Data

US 2014/0047588 P1 Feb. 13, 2014

(51) Int. Cl.
*A01H 5/00* (2006.01)

(52) U.S. Cl.
USPC ..... Plt./157

(58) Field of Classification Search
USPC ..... Plt./157
See application file for complete search history.

*Primary Examiner* — Susan McCormick Ewoldt
(74) *Attorney, Agent, or Firm* — Jondle Plant Sciences division of Swanson & Bratschun, L.L.C.

(57) ABSTRACT

A new and distinct variety of blueberry plant named 'DrisBlueSeven' particularly distinguished by having a very low chilling requirement, high productivity and very firm, large, sweet berries with intense blue color, is disclosed.

2 Drawing Sheets

Genus and species: *Vaccinium corymbosum* L.
Variety denomination: 'DrisBlueSeven'.

BACKGROUND OF THE NEW PLANT

The invention relates to a new and distinct blueberry variety designated 'DrisBlueSeven' and botanically known as *Vaccinium corymbosum* L. This new blueberry variety was discovered in Santa Cruz, Calif. in June 2001 and originated from a cross between the proprietary female parent blueberry plant 'MS122' (unpatented) and the male parent blueberry plant 'FL 92-166 N' (unpatented). The original seedling of the new variety was first asexually propagated at a nursery in Monterey, Calif. 'DrisBlueSeven' was subsequently asexually propagated and underwent further testing at a nursery in Santa Cruz, Calif. for twelve years. The present invention has been found to be stable and reproduce true to type through successive asexual propagations via softwood cuttings.

Plant Breeder's Rights for this variety have not been applied for. 'DrisBlueSeven' has not been made publicly available or sold more than one year prior to the filing date of this application.

SUMMARY OF THE INVENTION

The following are the most outstanding and distinguishing characteristics of this new cultivar when grown under normal horticultural practices in Santa Cruz, Calif.

1. A very low chilling requirement;
2. High productivity; and
3. Very firm, large, sweet berries with intense blue color.

DESCRIPTION OF THE PHOTOGRAPHS

This new blueberry plant is illustrated by the accompanying photographs which show fruit of the plant as well as the flowers and leaves. The colors shown are as true as can be reasonably obtained by conventional photographic procedures. The photographs are of plants that are 11 years old.

DESCRIPTION OF THE NEW CULTIVAR

Figure 1:
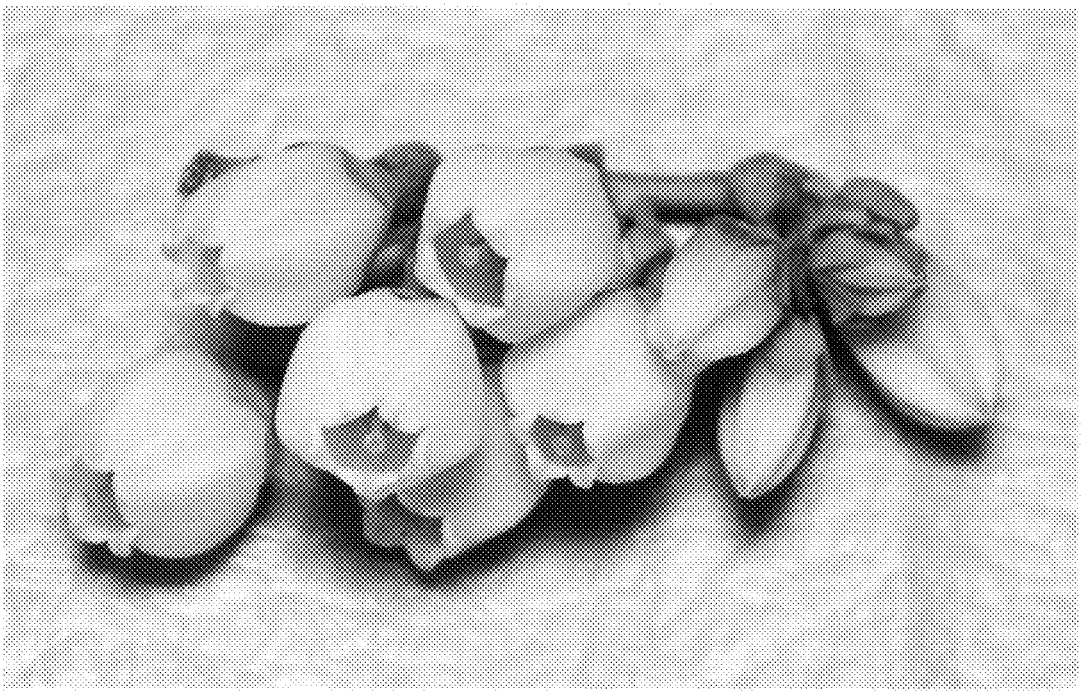
FIG. 1 shows a close-up of the mature flowers.
Figure 2:
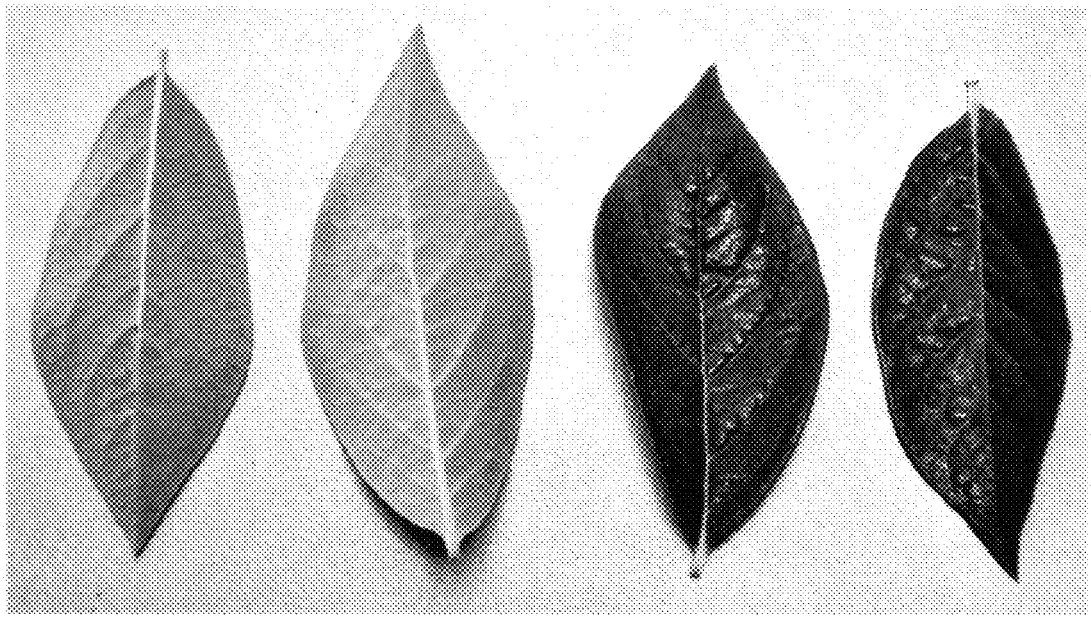
FIG. 2 shows a close-up of the leaves.
Figure 3:
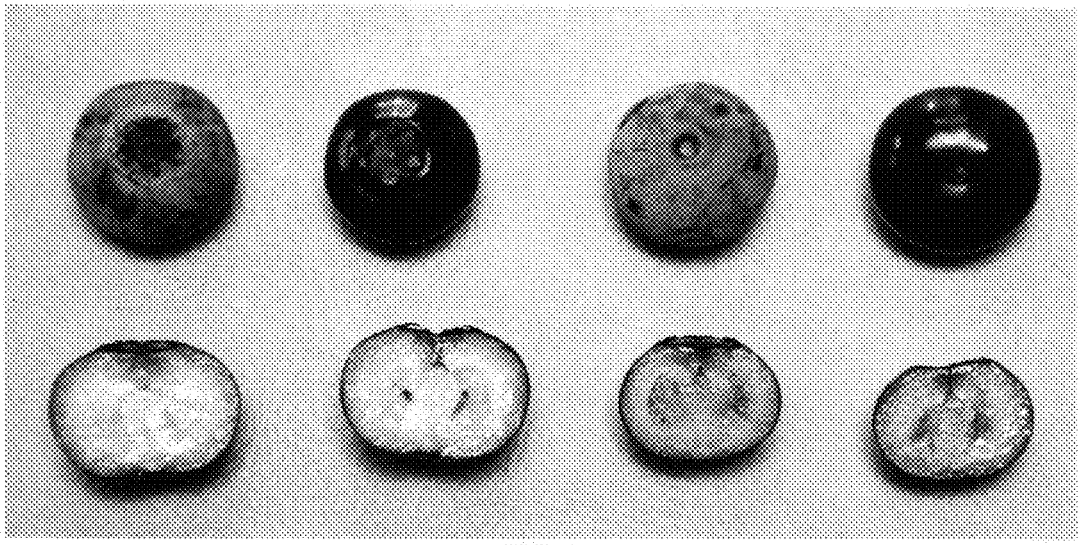
FIG. 3 shows a close-up of the whole fruit and a cross-section of the fruit.

The following detailed description sets forth the distinctive characteristics of 'DrisBlueSeven'. The data which define these characteristics is based on observations taken in Santa Cruz, Calif. from 2001-2012. This description is in accordance with UPOV terminology. Color designations, color descriptions, and other phenotypical descriptions may deviate from the stated values and descriptions depending upon variation in environmental, seasonal, climatic and cultural conditions. 'DrisBlueSeven' has not been observed under all possible environmental conditions. The botanical description of 'DrisBlueSeven' was taken from 11 year-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION

Classification:

*Family.*—Ericaceae.
*Botanical.*—*Vaccinium corymbosum* L.
*Common name.*—Blueberry.
*Variety name.*—'DrisBlueSeven'.

Parentage:

*Female parent*.—The proprietary blueberry plant 'MS122' (unpatented).

*Male parent*.—The blueberry plant 'FL 92-166 N' (unpatented).

Plant:

*Size*.—Large to very large.

*Height*.—163.5 cm.

*Width*.—123.5 cm.

*Length/width ratio*.—1.3.

*Plant vigor*.—Medium.

*Growth habit*.—Semi-erect.

*Productivity*.—High to very high.

*Cold hardiness*.—Medium.

*Chilling requirement*.—Very low; 150-250 chilling hours.

*Storability of fruit*.—1-2 weeks at 40 ° F. refrigeration.

*Propagation*.—Soft wood cuttings.

*Time of vegetative bud burst*.—Very early.

*Fruiting type*.—Only on one-year-old shoots.

*Cane renewal*.—Weak to medium.

*Internode length* (*upper half on one-year old shoot*).—30.05 mm

*One-year old canes* (*young canes*).—Length: 106.68 cm. Diameter at the base: 7.00 mm. Diameter at the tip: 3.83 mm. Texture: Smooth. Color (One-year old shoot, branch and canes): RHS 143C (Medium green).

*Five-year old canes* (*mature canes*).—Length: 141.34 cm. Diameter at the base: 21.54 mm. Diameter at the tip: 5.32 mm. Texture: Smooth. Color: RHS 145A (Light yellow-green).

Leaves:

*Length*.—Long; 6.30 cm.

*Width*.—Medium; 3.12 cm.

*Length/width ratio*.—2.0; longer than broad.

*Shape*.—Elliptic.

*Apex*.—Cuspidate.

*Base*.—Cuneate.

*Margin*.—Entire.

*Glossiness*.—Medium to glossy.

*Pubescence*.—Glabrous (Absent).

*Sheath*.—Absent.

*Arrangement*.—Alternate.

*Venation*.—Reticulate.

*Color*.—Upper surface: Dark; RHS 139A (Dark green). Lower surface: Medium; RHS 138B (Medium green).

*Appearance of leaf bud*.—Early.

*Internode length* (*one-year old shoot, upper half*).—Long; 24.63 mm.

Petiole:

*Length*.—4.5 mm.

*Diameter*.—1.75 mm.

*Color*.—RHS 145B (Light yellow-green).

Flowers:

*Length* (*excluding peduncle*).—Medium; 8.52 mm.

*Diameter*.—7.70 mm.

*Length/width ratio*.—1.1.

*Color*.—RHS 157D (Light green-white).

*Flower bud*.—Length: 6.2 mm. Width: 2.8 mm. Number of flowers per bud: 7. Color on immature buds: RHS 175C (Medium greyed-orange). Color on mature buds: RHS 142A (Light green).

*Petal width*.—4.50 mm.

*Fragrance*.—Very faint or absent.

*Time of beginning flowering on one-year shoot*.—Very early.

*Time of flowering* (50% *full bloom*).—Very early; March 6.

*Pedicel*.—Length: 7.48 mm. Diameter: 0.96 mm. Color: RHS 142B (Medium green).

*Corolla*.—Aperture diameter: 3.48 mm. Shape: Urceolate. Size of corolla tube: Medium. Corolla tube color: Weak; RHS 157D (Green-white). Ridges on tube: Present.

*Peduncle length*.—18.26 mm.

Reproductive organs:

*Style length* (*including stigma*).—Medium; 8.00 mm.

*Style color*.—RHS 144D (Light yellow-green).

*Ovary color*.—RHS 142B (Medium green).

*Pollen amount*.—Medium to high.

*Pollen color*.—RHS 4D (Light yellow).

*Anther color*.—RHS 164A (Medium greyed-orange).

Fruit:

*Size*.—Large.

*Length*.—13.07 mm.

*Width*.—18.69 mm.

*Length/width ratio*.—0.7.

*Fruit pedicel diameter*.—1.32 mm.

*Weight*.—3.0 g.

*Number of berries per cluster*.—7.

*Cluster density*.—Medium.

*Shape in longitudinal sections*.—Oblate.

*Intensity of green color* (*immature fruit with bloom*).—Medium; RHS 142B (Medium green).

*Color of skin* (*immature fruit without bloom*).—RHS 59A (Dark red-purple).

*Color of skin* (*mature fruit without bloom*).—RHS 103A (Dark blue).

*Color of skin* (*mature fruit with bloom*).—RHS 98D (Light blue).

*Intensity of bloom* (*mature fruit*).—Very strong.

*Attitude of sepals*.—Incurving and erect.

*Calyx*.—Diameter of basin: Large; 6.75 mm. Depth of basin: Shallow; 1.57 mm. Diameter/depth ratio: 4.3.

*Flesh color*.—RHS 145C (Yellow-green).

*Firmness*.—Very firm.

*Sweetness*.—Medium.

*Acidity*.—Medium.

*Market use*.—Fresh fruit market.

*Time of beginning of fruit ripening* (*one-year old shoots*).—Very early.

*Harvest season*.—Very early.

*Harvest interval*.—May 16-September 17.

Seeds:

*Length*.—1.62 mm.

*Width*.—1.06 mm.

*Length/width ratio*.—1.5.

*Abundance*.—Low to medium.

*Color*.—RHS 165B (Medium greyed-orange).

Resistance to pests and diseases: Data not available.

COMPARISON WITH PARENTAL AND COMMERCIAL VARIETIES

'DrisBlueSeven' differs from the female parent 'MS122' (unpatented) in that 'DrisBlueSeven' has a very low chilling requirement, whereas 'MS122' has a medium chilling requirement.

'DrisBlueSeven' differs from the male parent 'FL 92-166 N' (unpatented) in that 'DrisBlueSeven' has a very low chilling requirement, whereas 'FL 92-166 N' has a low chilling requirement.

'DrisBlueSeven' differs from the commercial variety 'DrisBlueOne' (U.S. Plant Pat. No. 20,449) in that 'DrisBlueSeven' has a semi-erect growth habit, a very early time of vegetative bud burst, and leaves with a cuspidate apex and cuneate base, whereas 'DrisBlueOne' has a bushy growth habit, a medium time of bud break, and leaves with a broadly acute apex and broadly acute to rounded base. Additionally, 'DrisBlueSeven' has a very low chilling requirement, whereas 'DrisBlueOne' has a medium chilling requirement.

'DrisBlueSeven' differs from the commercial variety 'DrisBlueTwo' (U.S. Plant Pat. No. 20,488), in that 'DrisBlueSeven' has leaves with an entire margin, oblate shaped berries, and a medium to high amount of pollen, whereas 'DrisBlueTwo' has leaves with serrulate margin, nearly spherical shaped berries and a sparse amount of pollen. Additionally, 'DrisBlueSeven' has a very low chilling requirement, whereas 'DrisBlueTwo' has a medium chilling requirement.

We claim:

1. A new and distinct variety of blueberry plant named 'DrisBlueSeven' as shown and described herein.

* * * * *